United States Patent [19]

Wendler et al.

[11] 4,094,878

[45] June 13, 1978

[54] CHEMICAL SYNTHESIS OF FLAVIPUCINE

[75] Inventors: Norman L. Wendler, Summit; Narindar N. Girotra, Fords, both of N.J.; Zbigniew S. Zelawski, deceased, late of Piscataway, N.J., by Maria W. Zelawski, administrator

[73] Assignee: Merck & Co., Inc., Rahway, N.J.

[21] Appl. No.: 798,288

[22] Filed: May 19, 1977

Related U.S. Application Data

[62] Division of Ser. No. 705,201, Jul. 14, 1976.

[51] Int. Cl.$^2$ ............................................. C07D 211/40
[52] U.S. Cl. .................................. 260/297 Z; 424/263
[58] Field of Search ........................ 260/297 R, 297 Z

[56] References Cited

PUBLICATIONS

Girota et al., J. Chem. Soc., Chem. Comm. 1976, pp. 566 to 567.
Chemical Abstracts, vol. 77, abst. No. 114194m (1972) (abst. of Findlay et al., J. Chem. Soc., Perkin Trans. 1 1972, pp. 2071–2074).
Findlay et al., Can. J. Chem. vol. 54, pp. 270 to 274 (1976).
Findlay et al., Synthetic Communications, vol. 3, pp. 355–358 (1973).

*Primary Examiner*—John D. Randolph
*Attorney, Agent, or Firm*—Frank M. Mahon; Edmunde D. Riedl; Julian S. Levitt

[57] ABSTRACT

A method for the total chemical synthesis of flavipucine employs the condensation of 4-hydroxy-6-methyl-2-pyridone with isobutylglyoxal in alkali alkoxide. The resulting alkali salt is acylated in both the 1' and 4 positions. Treatment of the 1',4-diacyloxy derivative with excess alkaline peroxide yields flavipucine.

4 Claims, No Drawings

CHEMICAL SYNTHESIS OF FLAVIPUCINE

This is a division of application Ser. No. 705,201 filed July 14, 1976.

DISCLOSURE OF THE INVENTION

This invention relates to a method for the total synthesis of the antibiotic (±) flavipucine together with its diastereoisomer (±) isoflavipucine. This invention pertains to the condensation of 4-hydroxy-6-methyl-2-pyridone with α-ketoaldehydes followed by acylation and hydrolytic oxidation to prepare 2-acyl-6-methyl-1-oxa-5-azaspiro-[2,5]-oct-6ene-4,8-diones. More particularly, this invention pertains to the condensation of 4-hydroxy-6-methyl-2-pyridone (I) with isobutylglyoxal followed by acylation and hydrolytic oxidation to prepare the compound of the structure V,

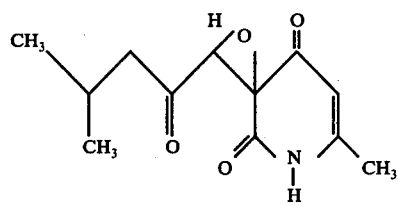

flavipucine. As used herein, the term flavipucine includes the various stereoisomers unless otherwise specified.

Flavipucine was isolated in 1968 from the fermentation of a strain of *Aspergillus flavipes*, and is active against gram-negative and gram-positive organisms. We have now achieved the total chemical synthesis of this antibiotic, which achievement enables production of the antibiotic independently of fermentation process thus eliminating inherent problems in such a process and the subsequent extraction procedures.

The synthesis is carried out in accordance with the following sequence of reactions:

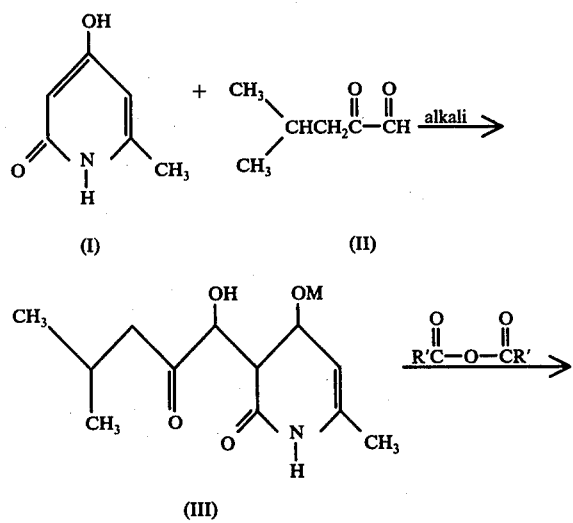

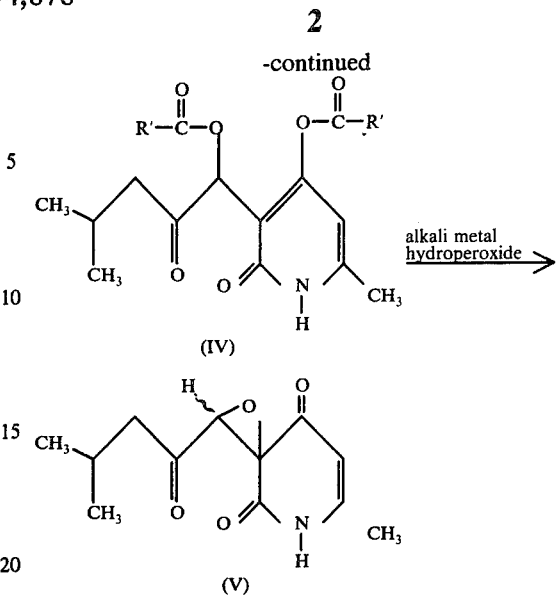

where R' is $C_1$ to $C_4$ alkyl, phenyl, or $C_1$ to $C_4$ alkyl substituted phenyl.

In carrying out the reactions, 4-hydroxy-6-methyl-2-pyridone (I) is condensed with glyoxal (II) in a suitable solvent including at least an equivalent of an alkali which includes alkali metal hydroxides, carbonates or $C_1$ to $C_4$ alkoxides at a temperature of from 10° to 40° C. and preferably 25° C. The term "alkali metal" as used herein means lithium, sodium, or potassium.

Suitable solvents include $C_1$ to $C_8$ alcohols, dimethylsulfoxide, dimethylformamide, acetonitrile and water but are not material to the reaction so long as they perform the solvating function without irreversibly reacting with either reactants or products.

The resulting alkali metal salt (III) is then acylated by reaction with acid anhydride, preferably acetic anhydride, at a temperature of from 0° to 25° C. without a solvent or in a neutral nonhydroxylic solvent to give the diester IV.

The diester IV is treated with at least an equivalent of strong base, e.g., alkali metal hydroxide in a tertiary $C_4$ to $C_{10}$ alkanol, e.g., t-butanol containing at least an equivalent of 30% hydrogen peroxide, suitably an excess, and preferably an eight equivalent excess. Alternatively, the diester IV can be treated with at least an equivalent of an alkali $C_4$ to $C_{10}$ t-alkoxide, preferably potassium t-butoxide in a similar alcoholic solvent, preferably a $C_4$ to $C_{10}$ t-alkanol such as t-butanol and at least an equivalent of a $C_4$ to $C_{10}$ t-alkyl hydroperoxide, e.g., t-butyl hydroperoxide at 0° to 25° C. for from 10 minutes to an hour although reaction is generally completed after one-half hour. This reaction accomplishes the incorporation of the epoxide function yielding (±) flavipucine together with its stereoisomer.

EXAMPLE 1

4-Hydroxy-6-methyl-3-(1'-hydroxy-2'oxo-4'-methylpentyl)-2-pyridone Sodium Salt To a stirred suspension of 3.128 g. (0.025 mole) of 4-hydroxy-6-methyl-2-pyridone in 300 ml. of methanol is added 1.350 g. (0.025 mole) of sodium methoxide followed by a solution of 3.542 g. (0.0268 mole) of isobutyl glyoxal in 25 ml. of methanol. After 16 hours at 25° C., the clear reaction mixture is concentrated to 30 ml. and diluted with 800 ml. of ether to precipitate the sodium salt. The solid product is collected by filtration, washed with more ether and evacuated to yield 7.10 g. of the colorless material.

EXAMPLE 2

4-Acetoxy-6-methyl-3-(1'-acetoxy-2'-oxy-4'-methylpentyl)-2-pyridone

Acetic anhydride (50 ml.) is added to a stirred sample (6.76 g.) of the sodium salt at 25° C. The latter dissolves with a slight exotherm followed by appearance of solid sodium acetate. After 16 hours at 25° C. the mixture is evaporated, flushed with toluene-heptane mixture three times. The residue is dissolved in dichloromethane, extracted with 10% aqueous potassium bicarbonate, dried and evaporated to give 7.840 g. of solid which is a mixture of diacetate and lactim triacetate in a ratio of 80:20 respectively as adjudged by NMR.

Recrystallization of the above solid from ether provides 5.170 g. of the crystalline diacetate, m.p. 129°–130° C.

Found: C, 59.91; H, 6.54; N, 4.16. Calc. for $C_{16}H_{21}O_6N$: C, 59.43; H, 6.55; N, 4.33.

The triacetate, present as a major component in the mother liquor is selectively converted to the diacetate my methanolysis.

EXAMPLE 3

(±) Flavipucine and (±) Isoflavipucine

To a stirred solution of 1.617 g. (0.005 mole) of the diacetate in 20 ml. of t-butyl hydroperoxide is added 5 ml. (0.005 mole) of 1M potassium t-butoxide and t-butanol at Ca ° C. in $N_2$. After two minutes the cooling bath is removed and stirring continued for one-half hour. The reaction mixture is evaporated to a thick paste, dissolved in dichloromethane, extracted with aqueous sodium sulfite and potassium bicarbonate, dried and evaporated to give 0.900 g. of semi-crystalline solid which on fractional crystalline from benzene provided 0.145 g. of (±) flavipucine (m.p. 154°–155° C., identical with natural (±) flavipucine in tlc., u.v., ir, NMR and mass spectra) and 0.200 g. of the diastereoisomer (±) isoflavipucine, m.p. 136°–138° C.

Found: C, 60.97; H, 6.15; N, 5.75. Calc. for $C_{12}H_{15}O_4N$: C, 60.75; H, 6.37; N, 5.90.

The mother liquors from fractional crystallization contained additional quantities of flavipucine and isoflavipucine.

EXAMPLE 4

Isobutylglyoxal

A solution of dimsyl sodium was prepared from 24 g. of a 50% sodium hydride oil dispersion and 250 cc. of anhydrous dimethyl sulfoxide at 65°–70° C. This solution was diluted with 250 cc of anhydrous tetrahydrofuran, chilled to 0° C. and treated with 32.5 g. of ethyl isovalerate. After stirring at 0° C. for 0.5 to 1 hour in a nitrogen atmosphere, the reaction mixture was poured into 2 liters of saturated sodium chloride solution, acidified with hydrochloric acid and the reaction product extracted with 1 to 1.5 liters of chloroform. The chloroform extract was washed with saturated sodium chloride solution, dried over anhydrous sodium sulfate and concentrated in vacuo to yield 38 g. of crude methyl sulfinyl methyl isobutyl ketone.

The above methyl sulfinyl methyl isobutyl ketone was dissolved in 200 cc. of dimethyl sulfoxide, diluted with 200 cc. of water and treated with 80 cc. of concentrated hydrochloric acid diluted to 200 cc with water. The reaction mixture was stirred at ambient temperature for 48 hours. At the end of this period, the reaction mixture was saturated with sodium chloride, extracted with chloroform and the chloroform extract dried over anhydrous sodium sulfate. Concentrations of the filtered chloroform solution in vacuo afforded 42 g. of crude isobutylglyoxal methylthiohemiacetal.

A mixture of 17 g. of isobutylglyoxal methylthiohemiacetal in 110 cc. of methylene chloride and 20 g. of copper acetate was stirred for 1 hour. At the conclusion of this time, the reaction mixture was filtered and the filtrate washed free of acid with dilute aqueous potassium bicarbonate solution and dried over anhydrous magnesium sulfate. Evaporation of the solvent provided isobutylglyoxal suitable for further transformations. Alternatively, this product could be distilled at 35° C. and 25 mm. pressure to yield a mixture of isobutylglyoxal and its hydrate as a yellow pungent oil.

What is claimed is:

1. A process for preparing (±) flavipucine and (±) isoflavipucine comprising reacting a diester of the formula:

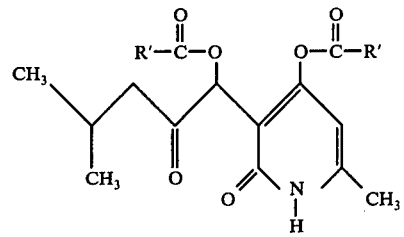

where R' is $C_1$ to $C_4$ alkyl, phenyl, or $C_1$ to $C_4$ alkyl substituted phenyl with at least one equivalent of alkali and a hydroperoxide ROOH where R is H or a $C_4$ to $C_{10}$ t-alkyl hydroperoxide to form the product

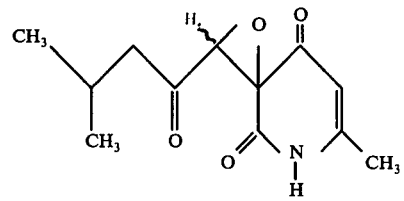

2. A process according to claim 1 where the peroxide is hydrogen peroxide.

3. A process according to claim 1 where the peroxide is t-butyl hydroperoxide.

4. A process according to claim 1 where each R' is methyl.

* * * * *